United States Patent [19]
DeFelice

[11] Patent Number: 5,962,020
[45] Date of Patent: Oct. 5, 1999

[54] COMPOSITION AND METHOD FOR PREVENTING AND/OR TREATING MICROALBUMINURIA

[76] Inventor: Stephen L. DeFelice, 235 Munsee Way, Westfield, N.J. 07090

[21] Appl. No.: 09/096,738

[22] Filed: Jun. 12, 1998

[51] Int. Cl.⁶ .............................. A61K 9/20; A61K 33/00; A61K 33/24; A61K 33/06
[52] U.S. Cl. ........................ 424/464; 424/600; 424/655; 424/682; 424/692; 514/52; 514/458; 514/866; 514/904; 514/905
[58] Field of Search .............................. 514/52, 458, 866, 514/904, 905; 424/464, 600, 692, 682, 655

[56] References Cited

U.S. PATENT DOCUMENTS

| | | | |
|---|---|---|---|
| 5,405,613 | 4/1995 | Rowland | 424/439 |
| 5,470,839 | 11/1995 | Laughlin et al. | 514/53 |
| 5,597,585 | 1/1997 | Williams et al. | 424/579 |
| 5,654,011 | 8/1997 | Jackson et al. | 424/635 |

OTHER PUBLICATIONS

Massry et al., "Massry and Glassock's Textbook of Nephrology", p. 1213, 1995.

*Primary Examiner*—Jose' G. Dees
*Assistant Examiner*—Marina Lamm
*Attorney, Agent, or Firm*—Watov & Kipnes, P.C.

[57] ABSTRACT

Composition and method of using the same for preventing or treating microalbuminuria in a warm blooded animal in which the composition contains effective amounts of vitamin E, folic acid, a magnesium-releasing compound, a chromium-releasing compound and vitamin B-12.

31 Claims, No Drawings

COMPOSITION AND METHOD FOR PREVENTING AND/OR TREATING MICROALBUMINURIA

FIELD OF THE INVENTION

The present invention is directed to a composition and method for preventing and/or treating microalbuminuria, a pathological condition where excessive amount of albumin is found in the urine. The composition includes microalbuminuria treating effective amounts of vitamin E, folic acid, a magnesium-containing compound, a chromium-containing compound and vitamin B-12.

BACKGROUND OF THE INVENTION

Albumin is a protein that is normally excreted in the urine in very low quantities. Microalbuminuria is a pathological condition where excessive albumin is found in the urine. Microalbuminuria is defined as the presence of from about 20 to 300 milligrams of protein in a 24-hour urine specimen or a urinary albumin excretion rate of from about 20 to 200 micrograms per minute.

The condition of microalbuminuria is quite high in diabetic patients. In comparison with Type I or juvenile diabetes, persistent microalbuminuria tends to occur closer to the time of diagnosis in Type II or adult onset diabetes. One explanation for this discrepancy is that the actual onset of disease and the diagnosis are typically concurrent in Type I but may be separated by years in Type II diabetes.

The most significant association that microalbuminuria has in patients with diabetes is premature death, primarily due to cardiovascular disease. Studies have shown an increase in cardiovascular-related mortality in patients with Type II diabetes who have microalbuminuria. One study has reported that more than two-thirds of patients with non-insulin dependent diabetes and microalbuminuria had died within 10 years; 7% from renal failure and 58% from cardiovascular disease. In another study, within less than 3½ years, 28% of the group with microalbuminuria had died and 80% of these deaths were due to cardiovascular disease. It is therefore believed that the presence of microalbuminuria is a risk factor associated with cardiovascular disease.

In addition to being an independent cardiovascular risk factor, microalbuminuria has been associated with increases in other known risk factors such as hypertension, abnormal lipid levels, blood coagulation disorders and possibly insulin resistance.

The current recommended treatment for microalbuminuria includes Ace-Inhibitors which are antihypertensive drugs. Ace-Inhibitors reduce microalbuminuria and have been reported to retard the progression of kidney failure. However, when the administration of Ace-Inhibitors ceases, microalbuminuria is likely to recur.

Vitamin/mineral compositions are known in the art to at least ensure that the user has the minimum essential requirements of the included vitamins and minerals. In some cases, some compositions are said to restore energetic balance or intensity, prevent or reduce life stage associated health risks such as menopause and the like. Examples of vitamins/mineral compositions are disclosed, for example, in D. Rowland, U.S. Pat. No. 5,405,613; A. H. Williams et al., U.S. Pat. No. 5,597,585; and S. D. Jackson, U.S. Pat. No. 5,654,011, each of which is incorporated herein by reference.

It would be a significant advance in the medical arts to provide a method of preventing and/or treating microalbuminuria so as to reduce the presence of albumin in the urine and the associated diseases for which microalbuminuria is a risk factor. It would be a further advance in the medical arts to provide a method of preventing and/or treating microalbuminuria which does not rely on costly antihypertensive drugs which can have serious side effects for the patient. It would be a further advance in the medical arts to provide a method of preventing and/or treating microalbuminuria which relies on safe ingredients well tolerated by most people. It would be a still further advance in the medical field to provide a method of preventing and/or treating microalbuminuria in which the ingredients can be administered only once a day by the patient to thereby increase patient compliance with the recommended therapy.

SUMMARY OF THE INVENTION

The present invention is generally directed to a composition and method of preventing and/or treating microalbuminuria to reduce the concentration of albumin in the urine and thereby reduce this risk factor implicated in a number of diseases including cardiovascular disease. The composition employs the combination of five vitamins/minerals in particular dosage amounts which together prevent and/or treat microalbuminuria and thereby prevent, reduce or eliminate the presence of albumin in the urine.

In particular, the composition of the present invention comprises vitamin E, folic acid, a magnesium-releasing compound, a chromium-releasing compound and vitamin B-12 in amounts effective in combination to at least prevent and/or treat albuminuria in a warm blooded animal. A method of preventing and/or treating warm blooded animals employing the present composition alone or in combination with other ingredients is also within the scope of the invention. The composition may contain in addition to the above-mentioned compounds as active ingredients conventional additives such as binders, carriers and the like.

The composition may be administered up to several times a day but is preferably administered once a day. The administration of the composition only once a day increases the level of patient compliance over therapies that may require multiple doses per day.

The preferred amount of each of the components of the composition for a daily dosage includes vitamin E in an amount of from about 50 to 2100 milligrams, folic acid in an amount of from about 50 to 2000 micrograms, an amount of a magnesium-releasing compound sufficient to provide from about 50 to 2000 milligrams of elemental magnesium to the patient, an amount of a chromium-releasing compound sufficient to provide from about 75 to 2100 micrograms of elemental chromium to the patient, and from about 10 to 2000 micrograms of vitamin B-12.

The composition can be administered in divided dosages up to several times a day. However, it is preferred that the composition be administered once a day to minimize missed dosages and to generally make it easier for the patient to receive the correct dosage everyday.

The magnesium-releasing compound employed in the present invention is one which readily provides elemental magnesium to the patient upon administration. The amount of the magnesium-releasing compound must be able to deliver from about 50 to 2000 milligrams of elemental magnesium on a daily basis. The magnesium-releasing compound should be non-toxic to the patient. Suitable magnesium-releasing compounds include magnesium salts such as, for example, magnesium oxide, magnesium gluconate and magnesium chloride.

The chromium-releasing compound must be sufficient to provide from about 75 to 2100 micrograms of elemental chromium to the patient. The chromium-releasing compound should be non-toxic to the patient. Suitable examples of chromium-releasing compounds are chromium salts such as chromium picolinate and chromium chloride. Chromium picolinate is the preferred chromium-releasing compound.

A preferred composition in accordance with the present invention includes vitamin E in an amount of from about 300 to 500 milligrams, folic acid in an amount of from about 0.8 to 1.2 milligrams, an amount of a magnesium-releasing compound sufficient to provide from about 200 to 400 milligrams of elemental magnesium, an amount of a chromium-releasing compound sufficient to provide from about 300 to 500 micrograms of elemental chromium, and vitamin B-12 in an amount of from about 0.8 to 1.2 milligrams.

A highly preferred composition in accordance with the present invention for daily dosage administration is about 400 milligrams of vitamin E, about one milligram of folic acid, an amount of a magnesium-releasing compound sufficient to provide about 300 milligrams of elemental magnesium, an amount of a chromium-releasing compound sufficient to provide about 400 micrograms of elemental chromium, and about one milligram of vitamin B-12.

The composition of the present invention can be administered in a variety of ways including orally, parenterally and sublingually. In a preferred form of the invention, the composition is contained within a capsule or tablet suitably formulated with standard pharmaceutical carriers and additives including, for example, binders, magnesium stearate, lactose, talc, sodium and/or disodium hydrogen phosphate, polyvinyl pyrrolidone, carboxymethyl cellulose, colorants, flavorants and the like. The composition can be formulated into a powder, compressed and formed into tablets or capsules in a conventional manner. The tablet or capsule is preferably administered orally once a day with the daily dosage requirements as previously described.

The present composition may be administered sublingually in chewable soft gelatin capsules in accordance with the procedures disclosed in U.S. Pat. No. 5,135,753, incorporated herein by reference.

EXAMPLE 400 mg of vitamin E, one mg of folic acid, 496 mg of magnesium oxide, 3.2 grams of chromium picolinate and one mg of vitamin B-12 are combined with talc, magnesium stearate, flavorant, sodium dihydrogen phosphate and disodium hydrogen phosphate and mixed followed by the addition of mannitol to form a powder.

The resulting powder is compressed using a single punch press to form individual tablets.

What is claimed:

1. A composition for treating microalbuminuria consisting essentially of a microalbuminuria treating effective amount of each of vitamin E, folic acid, a magnesium-releasing compound, a chromium-releasing compound and vitamin B-12 and a pharmaceutically acceptable excipient.

2. The composition of claim 1 wherein the amount of vitamin E is from about 50 to 2100 mg.

3. The composition of claim 1 wherein the amount of folic acid is from about 50 to 2000 ug.

4. The composition of claim 1 wherein the amount of the magnesium-releasing compound is sufficient to provide from about 50 to 2000 mg of elemental magnesium.

5. The composition of claim 1 wherein the amount of the chromium-releasing compound is sufficient to provide from about 75 to 2100 ug of elemental chromium.

6. The composition of claim 1 wherein the amount of vitamin B-12 is from about 10 to 2000 ug.

7. The composition of claim 1 wherein the magnesium-releasing is a magnesium salt.

8. The composition of claim 7 wherein the magnesium salt is magnesium oxide.

9. The composition of claim 1 wherein the chromium-releasing compound is chromium picolinate.

10. The composition of claim 1 wherein the amount of vitamin E is from about 50 to 2100 mg, the amount of folic acid is from about 50 to 2000 ug, the amount of the magnesium-releasing compound is sufficient to provide from about 50 to 2000 mg of elemental magnesium, the amount of the chromium-releasing compound is sufficient to provide from about 75 to 2100 ug of element chromium and the amount of vitamin B-12 is from about 10 to 2000 ug.

11. The composition of claim 10 wherein the amount of vitamin E is from about 300 to 500 mg, the amount of folic acid is from about 0.8 mg to 1.2 mg, the amount of the magnesium-releasing compound is sufficient to provide from about 200 to 400 mg of elemental magnesium, the amount of the chromium-releasing compound is sufficient to provide from about 300 to 500 ug of elemental chromium and the amount of vitamin B-12 is from about 0.8 to 1.2 mg.

12. The composition of claim 11 wherein the amount of vitamin E is about 400 mg, the amount of folic acid is about 1 mg, the amount of the magnesium-releasing compound is sufficient to provide about 300 mg of elemental magnesium, the amount of the chromium-releasing compound is sufficient to provide about 400 ug of elemental chromium and the amount of vitamin B-12 is about 1 mg.

13. The composition of claim 12 wherein the magnesium-releasing compound is a magnesium salt and the chromium-releasing compound is a chromium salt.

14. The compound of claim 13 wherein the magnesium salt is magnesium oxide and the chromium salt is chromium picolinate.

15. A method of treating microalbuminuria in a warm blooded animal comprising administering to said warm blooded animal a therapeutically effective amount of a composition consisting essentially of a microalbuminuria treating effective amount of each of vitamin E, folic acid, a magnesium-releasing compound, a chromium-releasing compound and vitamin B-12.

16. The method of claim 15 comprising administering the composition at least once per day.

17. The method of claim 16 comprising administering the composition once per day.

18. The method of claim 15 comprising administering the composition by a method selected from orally, parenterally and sublingually.

19. The method of claim 15 wherein the amount of vitamin E is from about 50 to 2100 mg.

20. The method of claim 15 wherein the amount of folic acid is from about 50 to 2000 ug.

21. The method of claim 15 wherein the amount of the magnesium-releasing compound is sufficient to provide from about 50 to 2000 mg of elemental magnesium.

22. The method of claim 15 wherein the amount of the chromium-releasing compound is sufficient to provide from about 75 to 2100 ug of elemental chromium.

23. The method of claim 15 wherein the amount of vitamin B-12 is from about 10 to 2000 ug.

24. The method of claim 15 wherein the magnesium-releasing is a magnesium salt.

25. The method of claim 24 wherein the magnesium salt is magnesium oxide.

26. The method of claim 15 wherein the chromium-releasing compound is chromium picolinate.

27. The method of claim 15 wherein the amount of vitamin E is from about 50 to 2100 mg, the amount of folic acid is from about 50 to 2000 ug, the amount of the magnesium-releasing compound is sufficient to provide from about 50 to 2000 mg of elemental magnesium, the amount of the chromium-releasing compound is sufficient to provide from about 75 to 2100 ug of element chromium and the amount of vitamin B-12 is from about 10 to 2000 ug.

28. The method of claim 27 wherein the amount of vitamin E is from about 300 to 500 mg, the amount of folic acid is from about 0.8 mg to 1.2 mg, the amount of the magnesium-releasing compound is sufficient to provide from about 200 to 400 mg of elemental magnesium, the amount of the chromium-releasing compound is sufficient to provide from about 300 to 500 ug of elemental chromium and the amount of vitamin B-12 is from about 0.8 to 1.2 mg.

29. The method of claim 28 wherein the amount of vitamin E is about 400 mg, the amount of folic acid is about 1 mg, the amount of the magnesium-releasing compound is sufficient to provide about 300 mg of elemental magnesium, the amount of the chromium-releasing compound is sufficient to provide about 400 ug of elemental chromium and the amount of vitamin B-12 is about 1 mg.

30. The method of claim 29 wherein the magnesium-releasing compound is a magnesium salt and the chromium-releasing compound is a chromium salt.

31. The method of claim 30 wherein the magnesium salt is magnesium oxide and the chromium salt is chromium picolinate.

* * * * *